(12) United States Patent
Isota et al.

(10) Patent No.: US 6,284,931 B1
(45) Date of Patent: Sep. 4, 2001

(54) PROCESS FOR PRODUCING 3, 3, 5-TRIMETHYLCYCLOHEXYLIDENEBIS PHENOL

(75) Inventors: Yoichiro Isota; Toru Nakaguchi; Hiroshi Takenaka; Kazuhiko Yao, all of Wakayama (JP)

(73) Assignee: Honshu Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 09/421,372

(22) Filed: Oct. 20, 1999

(30) Foreign Application Priority Data

Oct. 20, 1998 (JP) .................................................. 10-298204

(51) Int. Cl.⁷ ...................................................... C07L 39/17
(52) U.S. Cl. ............................................................. 568/721
(58) Field of Search ............................................... 568/721

(56) References Cited

U.S. PATENT DOCUMENTS

| 2,069,560 | 2/1937 | Rothrock . |
| 4,982,014 | 1/1991 | Freitag et al. . |
| 5,210,328 | 5/1993 | Freitag et al. . |
| 5,336,812 | 8/1994 | Salek et al. . |

FOREIGN PATENT DOCUMENTS

| 4121791A1 | 1/1993 | (DE) . |
| 0481287A2 | 4/1992 | (EP) . |
| 288634A | 3/1990 | (JP) . |
| 4282334A | 10/1992 | (JP) . |
| 9507250A | 7/1997 | (JP) . |
| 8505644A | 6/1998 | (JP) . |
| 5213803A | 8/1998 | (JP) . |
| WO9513259A1 | 5/1995 | (WO) . |
| WO9608458A1 | 3/1996 | (WO) . |

*Primary Examiner*—Michael L. Shippen
(74) *Attorney, Agent, or Firm*—Birch, Stewart, Kolasch & Birch, LLP

(57) ABSTRACT

A process for producing a 3,3,5-trimethylcyclohexylidenebisphenol, comprising pre-reacting a phenol (A), i.e., phenol whose 2- and 6-positions may be monosubstituted or disubstituted with an alkyl group having 1 to 4 carbon atoms, with 3,3,5-trimethylcyclohexanone (B) at a molar ratio ((A)/(B)) of 3 to 7 in the presence of an acid catalyst until 3,3,5-trimethylcyclohexanone (B) exhibits a degree of conversion of at least 90 mol %; adding the phenol (A) and/or an aromatic hydrocarbon (C) to the thus obtained reaction mixture; and post-reacting the resultant mixture. This process enables not only suppressing a rise of the viscosity of the reaction mixture but also obtaining the desired product at high yield. Therefore, this process is applicable to not only the productivity enhancement in batch processing but also a continuous reaction processing which has been regarded as being difficult.

8 Claims, No Drawings

PROCESS FOR PRODUCING 3, 3, 5-TRIMETHYLCYCLOHEXYLIDENEBISPHENOL

FIELD OF THE INVENTION

The present invention relates to a process for efficiently producing a 3,3,5-trimethylcyclohexylidenebisphenol which is useful as a starting material of various polymers such as aromatic polycarbonates, aromatic polyether sulfones, aromatic polyether ketones, aromatic ethers and aromatic ether imides. More particularly, the present invention relates to a process for producing a 3,3,5-trimethylcyclohexylidenebisphenol, which enables continuous reaction processing.

BACKGROUND OF THE INVENTION

Some processes which are commonly employed in the production of bisphenol and are based on the reaction of phenol with 3,3,5-trimethylcyclohexanone conducted in the presence of an acid and a thiol are known in the art as being available for the production of 3,3,5-trimethylcyclohexylidenebisphenols, especially 1,1-bis(4-hydroxyphenyl)-3,3,5-trimethylcyclohexane being a reaction product of phenol and 3,3,5-trimethylcyclohexanone.

For example, Japanese Patent Laid-open Publication No. 2(1990)-88634 discloses a process for producing 1,1-bis(4-hydroxyphenyl)-3,3,5-trimethylcyclohexane, which comprises reacting phenol with 3,3,5-trimethylcyclohexanone at a molar ratio (phenol/3,3,5-trimethylcyclohexanone) of 6/1 in the presence of a catalyst consisting of hydrogen chloride gas and an alkylmercaptan and removing unreacted phenol from the resultant reaction mixture by steam distillation.

Further, Published Japanese Translation of PCT Patent Applications from Other States, No. 8(1996)-505644 discloses a process for producing 1,1-bis(4-hydroxyphenyl)-3,3,5-trimethylcyclohexane, which comprises reacting phenol with 3,3,5-trimethylcyclohexanone in the presence of a reaction promoting catalyst consisting of a mixture of hydrochloric acid and an alkanethiol such as octanethiol to thereby obtain a reaction mixture containing 1,1-bis(4-hydroxyphenyl)-3,3,5-trimethylcyclohexane as an adduct of phenol and 3,3,5-trimethylcyclohexanone and separating 1,1-bis(4-hydroxyphenyl)-3,3,5-trimethylcyclohexane from the reaction mixture.

Still further, Published Japanese Translation of PCT Patent Applications from Other States, No. 9(1997)-507250 discloses a process for producing 1,1-bis(4-hydroxyphenyl)-3,3,5-trimethylcyclohexane, which comprises reacting a ketal or thioketal with phenol, the ketal or thioketal being to be synthesized from 3,3,5-trimethylcyclohexanone and a diol or mercaptoalcohol.

Moreover, Japanese Patent Laid-open Publication Nos. 5(1993)-213803 and 4(1992)-282334 disclose processes applicable to continuous processing, which comprise reacting a cyclohexanone with a phenol in the presence of an anhydrous insoluble cation exchange resin containing sulfonic groups (acidic anhydrous condensation catalyst) and β-mercaptopropionic acid or the like as a co-catalyst to thereby obtain a substituted cyclohexylidenebisphenol.

However, when 3,3,5-trimethylcyclohexanone is used as a starting material, the reaction is extremely slow (conversion of ketone 24 hr after the initiation of the reaction: 55%, see Comparative Example c) of Japanese Patent Laid-open Publication No. 4(1992)-282334). Further, the selectivity of 1,1-bis(4-hydroxyphenyl)-3,3,5-trimethylcyclohexane is low (selectivity: 72%, see Example 6 of Japanese Patent Laid-open Publication No. 5(1993)-213803).

A continuous reaction processing provides effective means for enhancing the efficiency in commercial production. Continuous feeding of a reaction mixture can be mentioned as one of the requirements for the continuous reaction processing.

However, 3,3,5-trimethylcyclohexylidenebisphenols, especially 1,1-bis(4-hydroxyphenyl)-3,3,5-trimethylcyclohexane, have the property of causing the viscosity of the reaction mixture to be abnormally high when the reaction is proceeded. Therefore, when the conventional processes described in the above publications are employed, either it is difficult to continuously feed a reaction mixture under conditions enhancing a reaction yield or, although a reaction mixture can be continuously fed, not only is the reaction rate extremely low but also the selectivity is poor.

Therefore, there is a demand for the development of a process for producing a 3,3,5-trimethylcyclohexylidenebisphenol, which process enables not only suppressing a rise of the viscosity of the reaction mixture but also obtaining the desired 3,3,5-trimethylcyclohexylidenebisphenol at high yield, and which process is applicable to not only the productivity enhancement in batch operation but also a continuous reaction processing.

OBJECT OF THE INVENTION

The present invention has been made with a view toward solving the above problems of the prior art. It is an object of the present invention to provide a process for producing a 3,3,5-trimethylcyclohexylidenebisphenol, which process enables not only suppressing a rise of the viscosity of the reaction mixture but also obtaining the desired 3,3,5-trimethylcyclohexylidenebisphenol at high yield, and which process is applicable to not only the productivity enhancement in batch operation but also a continuous reaction processing.

SUMMARY OF THE INVENTION

According to the present invention, there is provided a process for producing a 3,3,5-trimethylcyclohexylidenebisphenol, comprising reacting a phenol with 3,3,5-trimethylcyclohexanone in the presence of an acid catalyst, wherein a phenol (A) represented by the general formula:

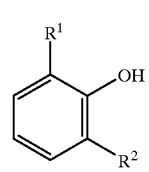

(I)

wherein each of $R^1$ and $R^2$ independently represents a hydrogen atom or an alkyl group having 1 to 4 carbon atoms, provided that $R^1$ and $R^2$ are not simultaneously alkyl groups having 4 carbon atoms, is pre-reacted with 3,3,5-trimethylcyclohexanone (B) at a molar ratio ((A)/(B)) of 3 to 7 in the presence of an acid catalyst until the 3,3,5-trimethylcyclohexanone (B) exhibits a degree of conversion of at least 90 mol %; and then the phenol (A) and/or an aromatic hydrocarbon (C) is added to the thus obtained reaction mixture and post-reacted to thereby obtain a 3,3,5-trimethylcyclohexylidenebisphenol.

The 3,3,5-trimethylcyclohexylidenebisphenol desired in the present invention is represented by the general formula:

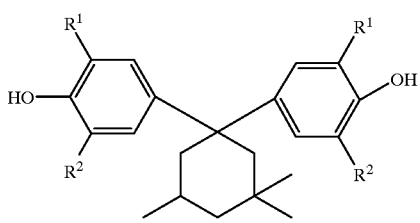

(II)

wherein each of $R^1$ and $R^2$ independently represents a hydrogen atom or an alkyl group having 1 to 4 carbon atoms, provided that $R^1$ and $R^2$ are not simultaneously alkyl groups having 4 carbon atoms.

It is preferred that the pre-reaction be performed by dropping a liquid mixture of the phenol (A) and 3,3,5-trimethylcyclohexanone (B) or a liquid mixture of the phenol (A), the aromatic hydrocarbon (C) and 3,3,5-trimethylcyclohexanone (B) into a system containing the phenol (A) or a liquid mixture of the phenol (A) and the aromatic hydrocarbon (C), water and an acid catalyst at 15 to 40° C. Further, it is preferred that the post-reaction be performed by adding the phenol (A) and/or the aromatic hydrocarbon (C) at one time or in divisions to the reaction mixture obtained by the pre-reaction.

In performing the post-reaction, the phenol (A) is preferably added to the reaction mixture obtained by the pre-reaction in such an amount that the molar ratio of total of the phenol (A) added in the pre-reaction and the pre-reaction to added 3,3,5-trimethylcyclohexanone (B) ((A)/(B)) is in the range of 5 to 10. Further, in performing the post-reaction, the aromatic hydrocarbon (C) is preferably added to the reaction mixture obtained by the pre-reaction in an amount of 10 to 30% by weight based on the reaction mixture obtained by the pre-reaction.

It is also preferred that the acid catalyst be a catalyst mixture composed of a mineral acid (a1) and a thiol (a2), the mineral acid (a1) being a hydrogen chloride gas and the thiol (a2) being an alkylmercaptan having 1 to 12 carbon atoms.

The phenol (A) is preferably phenol.

DETAILED DESCRIPTION OF THE INVENTION

The process for producing a 3,3,5-trimethylcyclohexylidenebisphenol according to the present invention will be described in detail below.

In the process for producing a 3,3,5-trimethylcyclohexylidenebisphenol according to the present invention, a phenol (A) is pre-reacted with 3,3,5-trimethylcyclohexanone (B) in the presence of an acid catalyst until the 3,3,5-trimethylcyclohexanone (B) exhibits a degree of conversion of at least 90 mol %; and then the phenol (A) and/or an aromatic hydrocarbon (C) is added to the thus obtained reaction mixture and post-reacted.

Acid catalyst

The acid catalyst for use in the present invention at least comprises a mineral acid (a1).

Suitable mineral acids (a1) are, for example, concentrated hydrochloric acid, hydrogen chloride gas, 60–98% sulfuric acid, 85% phosphoric acid and methanesulfonic acid. These can preferably be used either individually or in combination. Especially preferred the mineral acid (a1) is hydrogen chloride gas. Preferably, the air within a reaction system is replaced by an inert gas such as nitrogen gas and thereafter hydrogen chloride gas is continuously blown into the reaction system so that the interior of the reaction system is saturated.

The reaction between the phenol (A) and 3,3,5-trimethylcyclohexanone (B) can be catalyzed even with the use of the catalyst composed only of mineral acid (a1), and it is preferred, depending on the type of the phenol (A), that the catalyst be composed of the mineral acid (a1) and the thiol (a2).

The thiol (a2) for use in the present invention is an alkylmercaptan having 1 to 12 carbon atoms. For example, preferred use is made of any of methylmercaptan, ethylmercaptan, n-octylmercaptan and n-laurylmercaptan.

The reaction between the phenol (A) and 3,3,5-trimethylcyclohexanone (B) can be accelerated by the use of the catalyst composed of a catalyst mixture of mineral acid (a1) and thiol (a2).

The amount of thiol (a2) added is not particularly limited, and it is generally preferred that the thiol (a2) be added in an amount of 1 to 30 mol % based on the molar amount of 3,3,5-trimethylcyclohexanone (B).

Phenol (A)

The phenol (A) for use in the present invention is represented by the general formula (I):

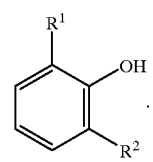

(I)

In the general formula (I), each of $R^1$ and $R^2$ independently represents a hydrogen atom or an alkyl group having 1 to 4 carbon atoms, provided that $R^1$ and $R^2$ are not simultaneously alkyl groups having 4 carbon atoms.

Examples of suitable alkyl groups having 1 to 4 carbon atoms represented by $R^1$ and $R^2$ include methyl, ethyl, n-propyl, isopropyl, n-butyl, isobutyl, s-butyl and t-butyl group.

Examples of suitable phenols (A) represented by the general formula (I) include:

phenol;

2-alkylphenols such as o-cresol, 2-ethylphenol, 2-n-propylphenol, 2-isopropylphenol, 2-n-butylphenol, 2-isobutylphenol, 2-s-butylphenol and 2-t-butylphenol; and 2,6-dialkylphenols such as 2,6-xylenol, 2-methyl-6-ethylphenol, 2-methyl-6-isopropylphenol, 2-methyl-6-isobutylphenol, 2-methyl-6-t-butylphenol, 2,6-diethylphenol, 2-ethyl-6-isopropylphenol, 2-ethyl-6-isobutylphenol, 2-ethyl-6-t-butylphenol, 2,6-di-n-propylphenol, 2-n-propyl-6-isopropylphenol, 2-n-propyl-6-isobutylphenol, 2-n-propyl-6-t-butylphenol, 2,6-diisopropylphenol, 2-isopropyl-6-isobutylphenol and 2-isopropyl-6-t-butylphenol. Of these, phenol and 2,6-xylenol which cause the reaction mixture at 40° C. or below to be a slurry are preferred.

When hydrogen chloride gas is used as the mineral acid (a1) for forming the acid catalyst, water is preferably added to the phenol (A) in a small amount, for example, 3 to 20% by weight based on the weight of the phenol (A) in order not only to lower the freezing point of the phenol (A) used in the pre-reaction step but also to increase the absorption of hydrogen chloride gas so that the reaction rate can be raised. When the phenol (A) used as a starting material is a phenol exhibiting a low water solubility and having a freezing point of 40° C. or higher, the phenol (A) is preferably used in the form of a liquid mixture with the aromatic hydrocarbon (C) described below.

In the pre-reaction step, the phenol (A) is generally introduced together with water (or aromatic hydrocarbon (C) described below) and optionally thiol (a2) in the reaction system before the blowing of hydrogen chloride gas thereinto. Further, after the blowing of hydrogen chloride gas, the phenol (A) is dropped in the form of a liquid mixture with 3,3,5-trimethylcyclohexanone (B) in the reaction system so that the phenol (A) reacts with 3,3,5-trimethylcyclohexanone (B).

The amount of the phenol (A) added in the pre-reaction step is 3 to 7, preferably 4 to 6, in terms of a molar ratio of the phenol (A)/3,3,5-trimethylcyclohexanone (B).

The aromatic hydrocarbon (C) may be introduced in the reaction system in the pre-reaction step. It is preferred that the amount of aromatic hydrocarbon (C) introduced be not more than 10% by weight based on the weight of reaction mixture.

Subsequently, in the post-reaction step, the phenol (A) can be added to the reaction mixture either alone or in combination with the aromatic hydrocarbon (C) after the conversion of 3,3,5-trimethylcyclohexanone (B) has reached 90 mol % or over in the pre-reaction. In place of the phenol (A), only the aromatic hydrocarbon (C) can be added to the reaction mixture.

The amount of the phenol (A) added after the conversion of 3,3,5-trimethylcyclohexanone (B) has reached 90 mol % or over is preferably such that the total molar amount of the phenol (A) added (the total phenol (A) consisting of the phenol (A) introduced in carrying out the pre-reaction, the phenol (A) dropped in the form of a liquid mixture with 3,3,5-trimethylcyclohexanone (B) in the reaction mixture and the phenol (A) added after the conversion of 3,3,5-trimethylcyclohexanone (B) has reached 90 mol % or over) is 5 to 10 times, especially 6 to 8 times, based on the molar amount of 3,3,5-trimethylcyclohexanone (B). When the amount of the phenol (A) added after the conversion of 3,3,5-trimethylcyclohexanone (B) has reached 90 mol % or over falls within the above range, not only can the rise of the viscosity of the reaction mixture be suppressed to thereby ensure efficient operation but also the desired 3,3,5-trimethylcyclohexylidenebisphenol can be obtained at high yield. The degree of conversion (%) of 3,3,5-trimethylcyclohexanone (TMC) is defined by the formula:

Conversion (%) of TMC={(amount of introduced TMC−amount of unreacted TMC)/amount of introduced TMC}×100.

When the aromatic hydrocarbon (C) is added to the reaction system of the post-reaction, it is preferred that the amount of the aromatic hydrocarbon (C) added be in the range of 10 to 30% by weight based on the reaction mixture obtained by the pre-reaction.

The addition of the phenol (A) and/or the aromatic hydrocarbon (C) in the post-reaction is to be made after the conversion of 3,3,5-trimethylcyclohexanone (B) has reached 90 mol % or over. When the phenol (A) and/or the aromatic hydrocarbon (C) is added to the reaction mixture in which the proportion of unreacted 3,3,5-trimethylcyclohexanone (B) is high, the reaction rate and the yield of desired 3,3,5-trimethylcyclohexylidenebisphenol are lowered. When the addition of the phenol (A) and/or aromatic hydrocarbon (C) is too late, the viscosity of the reaction mixture is unfavorably increased.

The phenol (A) to be added in the post-reaction may be added at one time at the initiation of the post-reaction, and it is preferred that the phenol (A) be added in divisions at the initiation of the post-reaction and during the post-reaction. When the phenol (A) to be added in the post-reaction is added in divisions and when the phenol (A) is phenol, the phenol is preferably added after the completion of the dropping of the liquid mixture of phenol (A) and 3,3,5-trimethylcyclohexanone (B) and within 1 hr of the initiation of the post-reaction, still preferably within 30 min of the initiation of the post-reaction.

3,3,5-trimethylcyclohexanone (B)

The 3,3,5-trimethylcyclohexanone (B) for use in the present invention is represented by the formula:

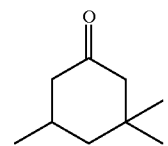

The 3,3,5-trimethylcyclohexanone (B) can be dropped either alone or in the form of a liquid mixture with the phenol (A) in the reaction system in which at least an acid catalyst is present. In the present invention, it is preferred that the 3,3,5-trimethylcyclohexanone (B) be used in the form of a liquid mixture with the phenol (A) optionally together with the aromatic hydrocarbon (C). The dropping thereof initiates the reaction (pre-reaction) of the phenol (A) with the 3,3,5-trimethylcyclohexanone (B).

The 3,3,5-trimethylcyclohexanone (B) is added in such an amount that the molar ratio of the phenol (A) added in the pre-reaction step ((A)/(B)) is in the range of 3 to 7, preferably 4 to 6.

Aromatic hydrocarbon (C)

The aromatic hydrocarbon (C) to be added to the reaction system in the pre-reaction and/or post-reaction of the present invention is, for example, selected from among alkylbenzenes such as toluene, xylene, mesitylene, pseudocumene, ethylbenzene, propylbenzene and butylbenzenes. These aromatic hydrocarbons are preferably used either individually or in the form of a mixture of two members thereof. Of these aromatic hydrocarbons, methylbenzenes such as toluene, xylene and mesitylene are preferred.

These aromatic hydrocarbons (C) can also suitably be used as a solvent in carrying out separation and purification of the desired product.

When the aromatic hydrocarbon (C) is added to the reaction system of pre-reaction and/or post-reaction, as mentioned above in the paragraph regarding phenol (A), it is preferred that the amount of aromatic hydrocarbon (C) added to the reaction mixture of pre-reaction be up to 10% by weight and that the amount of aromatic hydrocarbon (C) added in the post-reaction be in the range of 10 to 30% by weight based on the weight of reaction mixture obtained by the pre-reaction. When the aromatic hydrocarbon (C) is dropped or otherwise added in an amount satisfying the above requirements, not only can the rise of the viscosity of the reaction mixture be suppressed but also the desired 3,3,5-trimethylcyclohexylidenebisphenol can be obtained at high yield without lowering the reaction rate.

The aromatic hydrocarbon (C) to be added in the post-reaction may be added at one time at the initiation of the post-reaction, and it is preferred that the aromatic hydrocarbon (C) be added in divisions at the initiation of the post-reaction and during the post-reaction.

Reaction conditions

The reaction temperature during the pre-reaction and post-reaction of the present invention is preferably in the range of 15 to 40° C., still preferably 20 to 30° C. In the present invention, the reaction temperature is very important. When the reaction temperature is too low, the viscosity of the reaction mixture becomes extremely high to thereby disenable agitation. When the reaction temperature is too high, the formation of by-products is increased to thereby lower the yield of desired product. When the reaction temperature is in the range of 15 to 40° C., the reaction mixture can be agitated and the desired product can be obtained at high yield.

The pre-reaction and post-reaction are generally performed under atmospheric pressure, and any desired pressure can be employed in the reactions, which may be superatmospheric or reduced one.

A reaction mixture containing an adduct of 3,3,5-trimethylcyclohexylidenebisphenol/phenol (A) is obtained by performing the pre-reaction and post-reaction under the above reaction conditions. The existence yield of 3,3,5-trimethylcyclohexylidenebisphenol present in the reaction mixture is at least 85 mol %, usually 87 to 92%, based on the added 3,3,5-trimethylcyclohexanone (B).

3,3,5-trimethylcyclohexylidenebisphenol

In the present invention, a reaction mixture containing an adduct of 3,3,5-trimethylcyclohexylidenebisphenol/phenol (A) is obtained by performing the above pre-reaction and post-reaction. The 3,3,5-trimethylcyclohexylidenebisphenol desired in the present invention, which constitutes a component of the adduct, is represented by the general formula:

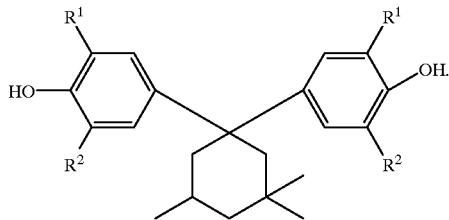

(II)

In the general formula (II), each of $R^1$ and $R^2$ has the same meaning as in the general formula (I), and independently represents a hydrogen atom or an alkyl group having 1 to 4 carbon atoms, provided that $R^1$ and $R^2$ are not simultaneously alkyl groups having 4 carbon atoms.

Examples of 3,3,5-trimethylcyclohexylidenebisphenols represented by the general formula (II) include:

1,1-bis(4-hydroxyphenyl)-3,3,5-trimethylcyclohexane,
1,1-bis(3-methyl-4-hydroxyphenyl)-3,3,5-trimethylcyclohexane,
1,1-bis(3-ethyl-4-hydroxyphenyl)-3,3,5-trimethylcyclohexane,
1,1-bis(3-n-propyl-4-hydroxyphenyl)-3,3,5-trimethylcyclohexane,
1,1-bis(3-isopropyl-4-hydroxyphenyl)-3,3,5-trimethylcyclohexane,
1,1-bis(3-n-butyl-4-hydroxyphenyl)-3,3,5-trimethylcyclohexane,
1,1-bis(3-isobutyl-4-hydroxyphenyl)-3,3,5-trimethylcyclohexane,
1,1-bis(3-s-butyl-4-hydroxyphenyl)-3,3,5-trimethylcyclohexane,
1,1-bis(3-t-butyl-4-hydroxyphenyl)-3,3,5-trimethylcyclohexane,
1,1-bis(3,5-dimethyl-4-hydroxyphenyl)-3,3,5-trimethylcyclohexane,
1,1-bis(3-methyl-5-ethyl-4-hydroxyphenyl)-3,3,5-trimethylcyclohexane,
1,1-bis(3-methyl-5-isopropyl-4-hydroxyphenyl)-3,3,5-trimethylcyclohexane,
1,1-bis(3-methyl-5-isobutyl-4-hydroxyphenyl)-3,3,5-trimethylcyclohexane,
1,1-bis(3-methyl-5-t-butyl-4-hydroxyphenyl)-3,3,5-trimethylcyclohexane,
1,1-bis(3,5-diethyl-4-hydroxyphenyl)-3,3,5-trimethylcyclohexane,
1,1-bis(3-ethyl-5-isopropyl-4-hydroxyphenyl)-3,3,5-trimethylcyclohexane,
1,1-bis(3-ethyl-5-isobutyl-4-hydroxyphenyl)-3,3,5-trimethylcyclohexane,
1,1-bis(3,5-di-n-propyl-4-hydroxyphenyl)-3,3,5-trimethylcyclohexane,
1,1-bis(3-n-propyl-5-isopropyl-4-hydroxyphenyl)-3,3,5-trimethylcyclohexane,
1,1-bis(3-n-propyl-5-isobutyl-4-hydroxyphenyl)-3,3,5-trimethylcyclohexane,
1,1-bis(3-n-propyl-5-t-butyl-4-hydroxyphenyl)-3,3,5-trimethylcyclohexane,
1,1-bis(3,5-diisopropyl-4-hydroxyphenyl)-3,3,5-trimethylcyclohexane,
1,1-bis(3-isopropyl-5-isobutyl-4-hydroxyphenyl)-3,3,5-trimethylcyclohexane, and
1,1-bis(3-isopropyl-5-t-butyl-4-hydroxyphenyl)-3,3,5-trimethylcyclohexane.

Purification

Purification of the 3,3,5-trimethylcyclohexylidenebisphenol desired in the present invention from the reaction mixture containing the adduct of 3,3,5-trimethylcyclohexylidenebisphenol/phenol (A), obtained through the above pre-reaction and post-reaction, can be conducted, for example, in the following manner.

First, after the completion of the reaction, the reaction mixture is neutralized with an alkaline aqueous solution of, for example, sodium hydroxide. Subsequently, unreacted phenol (A) is recovered by vacuum distillation, and recrystallization is carried out with the use of, for example, an aromatic hydrocarbon (C) or a solvent composed of a mixture of an alcohol and water. Thereafter, filtration and drying are carried out. Thus, the desired product can be obtained.

When the desired product forms an adduct with the starting material phenol (A), adduct crystals are separated from the neutralized liquid by filtration. The separated adduct crystals are recrystallized with the use of, for example, the aromatic hydrocarbon (C) or a solvent composed of a mixture of an alcohol and water, followed by filtration and drying. Thus, highly purified 3,3,5-trimethylcyclohexylidenebisphenol substantially not containing the phenol (A) can be obtained.

The isolation yield of thus purified 3,3,5-trimethylcyclohexylidenebisphenol is at least 70 mol %, usually 70 to 75 mol %, based on the molar amount of 3,3,5-trimethylcyclohexanone (B). This yield would be enhanced by about 5 to 10% by repeatedly employing the recrystallization filtrate.

When the product desired in the present invention is 1,1-bis(4-hydroxyphenyl)-3,3,5-trimethylcyclohexane, in the use of the conventional processes described in the prior art literature (published specifications) mentioned above in the paragraphs regarding the prior art, reacting phenol with 3,3,5-trimethylcyclohexanone under conditions enhancing reaction yield (no further addition of phenol) causes the viscosity of the reaction mixture to be abnormally high to thereby disenable continuous transfer of the reaction mixture (Comparative Example 3 given later in this specification). Furthermore, increasing the amount of phenol (high molar ratio) added to the reaction system (Comparative Example 2 given later in this specification), or raising the reaction temperature (Comparative Example 1 given later in this specification), or adding a diluent solvent (Comparative Example 4 given later in this specification), although lowering the viscosity of the reaction mixture, causes the amount of by-products to increase to thereby render the yield of desired 1,1-bis(4-hydroxyphenyl)-3,3,5-trimethylcyclohexane extremely low. The use of an ion exchange resin as a catalyst, although not increasing the viscosity of the reaction mixture, also lowers the yield of desired product (Comparative Example 5 given later in this specification).

By contrast, in the process for producing a 3,3,5-trimethylcyclohexylidenebisphenol according to the present invention, even if the same amounts of starting materials as in the comparative examples are employed, the viscosity of the reaction mixture is lowered with the yield of desired product enhanced by employing the method in which starting material phenol (A) is added in divisions, i.e. added partly to the pre-reaction system and partly to the post-reaction system, or the method in which phenol (A) is added to the pre-reaction system and aromatic hydrocarbon (C) added to the post-reaction system. The reason, although not yet elucidated, is assumed to be that the molar amount of phenol undergoing an addition reaction with 1,1-bis(4-hydroxyphenyl)-3,3,5-trimethylcyclohexane is changed, specifically reduced, when 1,1-bis(4-hydroxyphenyl)-3,3,5-trimethylcyclohexane formed by the reaction forms an adduct with unreacted phenol.

EFFECT OF THE INVENTION

The process for producing a 3,3,5-trimethylcyclohexylidenebisphenol according to the present invention enables not only suppressing a rise of the viscosity of the reaction mixture but also obtaining the desired 3,3,5-trimethylcyclohexylidenebisphenol at high yield. Therefore, this process is applicable to not only the productivity enhancement in batch processing but also a continuous reaction processing which has been regarded as being difficult.

EXAMPLE

The present invention will further be illustrated below with reference to the following Examples which in no way limit the scope of the invention.

In the tracing of reaction, the residual amount of unreacted 3,3,5-trimethylcyclohexanone (B) was analyzed by gas chromatography (GC analysis), and the amount of desired product having been formed by the reaction was determined by liquid chromatography (HPLC analysis).

In the following Examples and Comparative Examples, the existence yield of desired product is expressed by mol % based on the starting material 3,3,5-trimethylcyclohexanone (B).

Example 1

62.5 g (0.665 mol) of phenol, 7.6 g of water and 4.2 g of octylmercaptan were charged into a 1000 ml four-necked flask equipped with an agitator, a torque meter, a thermometer, a dropping funnel and a reflux condenser. While maintaining the internal temperature at 20 to 30° C., the interior of reaction system was purged with nitrogen gas and hydrogen chloride gas was blown thereinto until the system interior was saturated with hydrogen chloride gas.

While maintaining the internal temperature at 25 to 30° C., a liquid mixture of 78.5 g (0.835 mol) of phenol and 42.0 g (0.300 mol) of 3,3,5-trimethylcyclohexanone was dropped into the flask contents over a period of 3 hr to carry out a reaction. Before the dropping reaction, the flask contents were in the form of a solution and the agitator torque was 1.2 kg/cm. However, at the completion of the dropping reaction, the flask contents were in the form of a slurry and the agitator torque was 2.5 kg/cm. Further, at the completion of the dropping reaction, the conversion of 3,3,5-trimethylcyclohexanone was 97.4 mol %.

After the completion of the dropping reaction, 28.2 g (0.30 mol) of phenol was added to the reaction mixture, and a post-reaction was performed for 3 hr. At the completion of the post-reaction, the agitator torque was 3.0 kg/cm. Thus, the viscosity of reaction mixture at the completion of the post-reaction was approximately the same as that of reaction mixture at the completion of the dropping reaction.

A 16% aqueous solution of NaOH was added to the resultant reaction mixture to thereby effect a neutralization to a pH value of 5 to 6. This caused the agitator torque to change to the same 1.2 kg/cm as exhibited by the solution prior to the dropping reaction.

After the completion of the reactions, the reaction mixture was analyzed by gas chromatography. It was found that unreacted 3,3,5-trimethylcyclohexanone (TMC) was substantially absent in the reaction mixture. Further, liquid chromatography analysis showed that the existence yield of desired 1,1-bis(4-hydroxyphenyl)-3,3,5-trimethylcyclohexane was 90.7 mol %. This 1,1-bis(4-hydroxyphenyl)-3,3,5-trimethylcyclohexane was present in the form of an adduct with phenol.

Example 2

62.5 g (0.665 mol) of phenol, 7.7 g of water and 5.8 g of dodecylmercaptan were charged into a 1000 ml four-necked flask having the same equipment as in Example 1. While maintaining the internal temperature at 20 to 30° C., the interior of reaction system was purged with nitrogen gas and hydrogen chloride gas was blown thereinto until the system interior was saturated with hydrogen chloride gas.

While maintaining the internal temperature at 25 to 30° C., a liquid mixture of 78.5 g (0.835 mol) of phenol and 42.0 g (0.300 mol) of 3,3,5-trimethylcyclohexanone was dropped into the flask contents over a period of 3 hr to carry out a reaction.

Before the dropping reaction, the flask contents were in the form of a solution and the agitator torque was 1.7 kg/cm. However, at the completion of the dropping reaction, the flask contents were in the form of a slurry and the agitator torque was 4.3 kg/cm. Further, at the completion of the dropping reaction, the conversion of 3,3,5-trimethylcyclohexanone was 96.0 mol %.

After the completion of the dropping reaction, 28.2 g (0.30 mol) of phenol was added to the reaction mixture, and a post-reaction was performed for 5 hr. At the completion of the post-reaction, the agitator torque was 4.5 kg/cm. Thus, the viscosity of reaction mixture at the completion of the post-reaction was approximately the same as that of reaction mixture at the completion of the dropping reaction.

A 16% aqueous solution of NaOH was added to the resultant reaction mixture to thereby effect a neutralization to a pH value of 5 to 6. This caused the agitator torque to change to 1.7 kg/cm. Thus, the viscosity of reaction mixture after the neutralization was the same as exhibited by the solution prior to the dropping reaction.

After the completion of the reactions, the reaction mixture was analyzed by gas chromatography. It was found that the conversion of 3,3,5-trimethylcyclohexanone (TMC) was 99 mol % or higher. Further, liquid chromatography analysis showed that the existence yield of desired 1,1-bis(4-hydroxyphenyl)-3,3,5-trimethylcyclohexane was 91.0 mol %. This 1,1-bis(4-hydroxyphenyl)-3,3,5-trimethylcyclohexane was present in the form of an adduct with phenol.

Example 3

37.2 g (0.396 mol) of phenol and 9.0 g of water were charged into a 1000 ml four-necked flask having the same equipment as in Example 1. While maintaining the internal temperature at 20 to 30° C., the interior of reaction system was purged with nitrogen gas and hydrogen chloride gas was blown thereinto until the system interior was saturated with hydrogen chloride gas. Thereafter, 3.8 g of a 10% aqueous methylmercaptan sodium hydroxide solution was charged into the reaction system.

While maintaining the internal temperature at 25 to 30° C., a liquid mixture of 110.4 g (1.174 mol) of phenol and 42.2 g (0.301 mol) of 3,3,5-trimethylcyclohexanone was dropped into the flask contents over a period of 3 hr to carry out a reaction.

Before the dropping reaction, the flask contents were in the form of a solution and the agitator torque was 1.1 kg/cm. However, at the completion of the dropping reaction, the flask contents were in the form of a slurry and the agitator torque was 1.7 kg/cm. Further, at the completion of the dropping reaction, the conversion of 3,3,5-trimethylcyclohexanone was 97.0 mol %.

After the completion of the dropping reaction, 22.3 g (0.237 mol) of phenol was added to the reaction mixture, and a post-reaction was performed for 5 hr. At the completion of the post-reaction, the agitator torque was 3.5 kg/cm.

A 16% aqueous solution of NaOH was added to the resultant reaction mixture to thereby effect a neutralization to a pH value of 5 to 6. This caused the agitator torque to change to 1.2 kg/cm. Thus, the viscosity of reaction mixture after the neutralization was approximately the same as exhibited by the solution prior to the dropping reaction.

After the completion of the reactions, the reaction mixture was analyzed by gas chromatography. It was found that the conversion of 3,3,5-trimethylcyclohexanone (TMC) was 99 mol % or higher. Further, liquid chromatography analysis showed that the existence yield of desired 1,1-bis(4-hydroxyphenyl)-3,3,5-trimethylcyclohexane was 90.5 mol %. This 1,1-bis(4-hydroxyphenyl)-3,3,5-trimethylcyclohexane was present in the form of an adduct with phenol.

Example 4

90.0 g (0.957 mol) of phenol, 7.6 g of water and 4.2 g of octylmercaptan were charged into a 1000 ml four-necked flask having the same equipment as in Example 1. While maintaining the internal temperature at 20 to 30° C., the interior of reaction system was purged with nitrogen gas and hydrogen chloride gas was blown thereinto until the system interior was saturated with hydrogen chloride gas.

While maintaining the internal temperature at 25 to 30° C., a liquid mixture of 113.0 g (1.202 mol) of phenol and 42.0 g (0.300 mol) of 3,3,5-trimethylcyclohexanone was dropped into the flask contents over a period of 3 hr to carry out a reaction.

Before the dropping reaction, the flask contents were in the form of a solution and the agitator torque was 0.9 kg/cm. However, at the completion of the dropping reaction, the flask contents were in the form of a slurry and the agitator torque was 1.2 kg/cm. Further, at the completion of the dropping reaction, the conversion of 3,3,5-trimethylcyclohexanone was 95.0 mol %.

After the completion of the dropping reaction, 28.5 g of toluene was added to the reaction mixture to initiate a post-reaction. Further, 18.0 g of toluene was added 1 hr later, and the post-reaction was performed for a total of 5 hr. At the completion of the post-reaction, the agitator torque was 1.0 kg/cm. Thus, the viscosity of reaction mixture at the completion of the post-reaction was approximately the same as exhibited by the solution prior to the dropping reaction.

A 16% aqueous solution of NaOH was added to the resultant reaction mixture to thereby effect a neutralization to a pH value of 5 to 6. After the completion of the reactions, the reaction mixture was analyzed by gas chromatography. It was found that the conversion of 3,3,5-trimethylcyclohexanone (TMC) was 99 mol % or higher. Further, liquid chromatography analysis showed that the existence yield of desired 1,1-bis(4-hydroxyphenyl)-3,3,5-trimethylcyclohexane was 88.9 mol %. This 1,1-bis(4-hydroxyphenyl)-3,3,5-trimethylcyclohexane was present in the form of an adduct with phenol.

Example 5

40.3 g (0.33 mol) of 2,6-xylenol, 12.0 g of toluene and 4.2 g of octylmercaptan were charged into a 1000 ml four-necked flask having the same equipment as in Example 1. While maintaining the internal temperature at 30° C., the interior of reaction system was purged with nitrogen gas and hydrogen chloride gas was blown thereinto until the system interior was saturated with hydrogen chloride gas.

While maintaining the internal temperature at 30° C., a liquid mixture of 119.5 g (0.98 mol) of 2,6-xylenol and 42.2 g (0.301 mol) of 3,3,5-trimethylcyclohexanone was dropped into the flask contents over a period of 3 hr to carry out a reaction.

Before the dropping reaction, the flask contents were in the form of a solution and the agitator torque was 1.8 kg/cm. However, 30 min after the completion of the dropping reaction, the agitator torque was 2.2 kg/cm. Further, at that time, the conversion of 3,3,5-trimethylcyclohexanone was 93.1 mol %.

At that time, 24.1 g (0.20 mol) of 2,6-xylenol was added to the reaction mixture to carry on a post-reaction. The post-reaction was performed for 5 hr. At the completion of the post-reaction, the agitator torque was 2.4 kg/cm. Thus, the viscosity of reaction mixture at the completion of the post-reaction was approximately the same as that of reaction mixture obtained 30 min after the completion of the dropping reaction.

A 16% aqueous solution of NaOH was added to the resultant reaction mixture to thereby effect a neutralization to a pH value of 5 to 6. After the completion of the reactions, the reaction mixture was analyzed by gas chromatography. It was found that the conversion of 3,3,5-trimethylcyclohexanone (TMC) was 99 mol % or higher. Further, liquid chromatography analysis showed that the existence yield of desired 1,1-bis(3,5-dimethyl-4-hydroxyphenyl)-3,3,5-trimethylcyclohexane was 87.1 mol %. This 1,1-bis(3,5-dimethyl-4-hydroxyphenyl)-3,3,5-trimethylcyclohexane was present in the form of an adduct with 2,6-xylenol.

Comparative Example 1

62.8 g (0.668 mol) of phenol and 4.2 g of octylmercaptan were charged into a 1000 ml four-necked flask having the same equipment as in Example 1. While maintaining the internal temperature at 50° C., the interior of reaction system was purged with nitrogen gas and 33.9 g (0.33 mol) of concentrated hydrochloric acid was added thereto. While maintaining the internal temperature at 50° C., a liquid mixture of 78.5 g (0.835 mol) of phenol and 42.0 g (0.300 mol) of 3,3,5-trimethylcyclohexanone was dropped into the flask contents over a period of 3 hr to carry out a reaction.

After the completion of the dropping reaction, without adding phenol, the reaction was continued at 50° C. for 5 hr. The agitator torque after the reaction was substantially unchanged from that before the reaction, which was as low as 1.2 kg/cm. Liquid chromatography analysis of the reaction mixture showed that the existence yield of desired 1,1-bis(4-hydroxyphenyl)-3,3,5-trimethylcyclohexane was very low, 45 mol %.

Comparative Example 2

94.0 g (1.0 mol) of phenol, 14.1 g of water and 2.2 g of octylmercaptan were charged into a 1000 ml four-necked flask having the same equipment as in Example 1. While maintaining the internal temperature at 30° C., the interior of reaction system was purged with nitrogen gas and hydrogen chloride gas was blown thereinto until the system interior was saturated with hydrogen chloride gas.

While maintaining the internal temperature at 30° C., a liquid mixture of 94 g (1.0 mol) of phenol and 14.0 g (0.10 mol) of 3,3,5-trimethylcyclohexanone was dropped into the flask contents over a period of 3 hr to carry out a reaction.

After the completion of the dropping reaction, without adding phenol, the reaction was continued at 30° C. for 5 hr. The agitator torque after the reaction was substantially unchanged from that before the reaction, which was as low as 1.2 kg/cm. Liquid chromatography analysis of the reaction mixture showed that the existence yield of desired 1,1-bis(4-hydroxyphenyl)-3,3,5-trimethylcyclohexane was very low, 27.6 mol % (based on TMC).

Comparative Example 3

75.2 g (0.80 mol) of phenol, 11.3 g of water and 5.6 g of octylmercaptan were charged into a 1000 ml four-necked flask having the same equipment as in Example 1. While maintaining the internal temperature at 30° C., the interior of reaction system was purged with nitrogen gas and hydrogen chloride gas was blown thereinto until the system interior was saturated with hydrogen chloride gas.

While maintaining the internal temperature at 30° C., a liquid mixture of 75.2 g (0.80 mol) of phenol and 56.0 g (0.400 mol) of 3,3,5-trimethylcyclohexanone was dropped into the flask contents over a period of 3 hr to carry out a reaction. At the completion of the dropping reaction, the agitator torque was 2.5 kg/cm.

After the completion of the dropping reaction, without adding phenol, the reaction was continued at 30° C. for 3 hr. The agitator torque after the completion of the reaction was increased to 6.0 kg/cm, thereby disenabling further agitation.

The resultant reaction mixture was neutralized with an aqueous solution of NaOH. Liquid chromatography analysis of the reaction mixture showed that the existence yield of desired 1,1-bis(4-hydroxyphenyl)-3,3,5-trimethylcyclohexane was 84.5 mol %.

Comparative Example 4

94 g (1.0 mol) of phenol, 14.1 g of water, 2.2 g of octylmercaptan and 47 g of toluene were charged into a 1000 ml four-necked flask having the same equipment as in Example 1. While maintaining the internal temperature at 30° C., the interior of reaction system was purged with nitrogen gas and hydrogen chloride gas was blown thereinto until the system interior was saturated with hydrogen chloride gas.

While maintaining the internal temperature at 30° C., a liquid mixture of 75.2 g (0.80 mol) of phenol and 56.0 g (0.400 mol) of 3,3,5-trimethylcyclohexanone was dropped into the flask contents over a period of 3 hr to carry out a reaction.

After the completion of the dropping reaction, without adding phenol, the reaction was continued at 30° C. for 5 hr. The agitator torque at the completion of the reaction was 1.5 kg/cm, indicating a viscosity slightly higher than that prior to the dropping reaction.

A 16% aqueous solution of NaOH was added to the resultant reaction mixture to thereby effect a neutralization to a pH value of 5 to 6, and the reaction mixture after the completion of the reactions was analyzed by gas chromatography. It was found, however, that 15% of unreacted 3,3,5-trimethylcyclohexanone (TMC) was present in the reaction mixture. Further, liquid chromatography analysis of the reaction mixture showed that the existence yield of desired 1,1-bis(4-hydroxyphenyl)-3,3,5-trimethylcyclohexane was as low as 78 mol %.

Comparative Example 5

112.8 g (1.20 mol) of phenol, 6.4 g (0.06 mol) of β-mercaptopropionic acid, 0.6 g of water and 60 g of cation exchange resin (Lewatitk1131) washed with methanol in advance were charged into a 500 ml four-necked flask having the same equipment as in Example 1. 5.6 g (0.04 mol) of 3,3,5-trimethylcyclohexanone was added to the flask contents under agitation, and the reaction at 40° C. was compared with that at 60° C.

Although the viscosity of reaction mixture after the reaction was substantially unchanged from that prior to the reaction, as specified in Table 1, the reaction rate was very low at 40° C. while the selectivity of 1,1-bis(4-hydroxyphenyl)-3,3,5-trimethylcyclohexane was low at 60° C. Thus, at both reaction temperatures, the existence yield of desired product was very low.

TABLE 1

| Reaction temp. (° C.) | Reaction temp. (hr) | Conversion of TMC (%) | Selectivity (%) | Yield (mol %) |
| --- | --- | --- | --- | --- |
| 40 | 24 | 22 | 88 | 19.4 |
| 40 | 48 | 34 | 83 | 28.2 |
| 60 | 9 | 47 | 65 | 30.6 |
| 60 | 24 | 50 | 53 | 26.5 |

NOTE
Yield: yield based on 3,3,5-trimethylcyclahexanone (TMC)

What is claimed is:
1. A process for producing a 3,3,5-trimethylcyclohexylidenebisphenol, comprising reacting a phenol with 3,3,5-trimethylcyclohexanone in the presence of an acid catalyst, wherein a phenol (A) represented by the general formula:

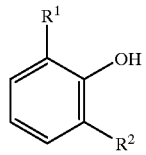

(I)

wherein each of $R^1$ and $R^2$ independently represents a hydrogen atom or an alkyl group having 1 to 4 carbon atoms, provided that $R^1$ and $R^2$ are not simultaneously alkyl groups having 4 carbon atoms, is pre-reacted with 3,3,5-trimethylcyclohexanone (B) at a molar ratio ((A)/(B)) of 3 to 7 in the presence of an acid catalyst until the 3,3,5-trimethylcyclohexanone (B) exhibits a degree of conversion of at least 90 mol %; and then the phenol (A) and/or an aromatic hydrocarbon (C) is added to the thus obtained reaction mixture and post-reacted to thereby obtain a 3,3,5-trimethylcyclohexylidenebisphenol represented by the general formula:

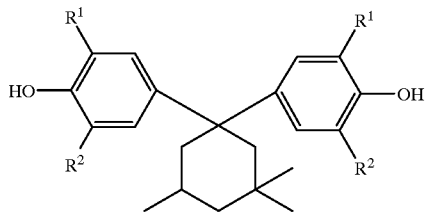

[II]

wherein each of $R^1$ and $R^2$ independently represents a hydrogen atom or an alkyl group having 1 to 4 carbon atoms, provided that $R^1$ and $R^2$ are not simultaneously alkyl groups having 4 carbon atoms.

2. The process as claimed in claim 1, wherein the pre-reaction is performed by dropping a liquid mixture of the phenol (A) and 3,3,5-trimethylcyclohexanone (B) or a liquid mixture of the phenol (A), the aromatic hydrocarbon (C) and 3,3,5-trimethylcyclohexanone (B) into a system containing the phenol (A) or a liquid mixture of the phenol (A) and the aromatic hydrocarbon (C), water and an acid catalyst at 15 to 40° C.

3. The process as claimed in claim 1, wherein in the pre-reaction the amount of the aromatic hydrocarbon (C) contained in the reaction mixture is not greater than 10% by weight.

4. The process as claimed in claim 1, wherein the post-reaction is performed by adding the phenol (A) and/or the aromatic hydrocarbon (C) at one time or in divisions to the reaction mixture obtained by the pre-reaction.

5. The process as claimed in claim 1, wherein, in performing the post-reaction, the phenol (A) is added to the reaction mixture obtained by the pre-reaction in such an amount that the molar ratio of total of the phenol (A) added in the pre-reaction and the pre-reaction to added 3,3,5-trimethylcyclohexanone (B) ((A)/(B)) is in the range of 5 to 10.

6. The process as claimed in claim 1, wherein, in performing the post-reaction, the aromatic hydrocarbon (C) is added to the reaction mixture obtained by the pre-reaction in an amount of 10 to 30% by weight based on the reaction mixture obtained by the pre-reaction.

7. The process as claimed in claim 1, wherein the acid catalyst is a catalyst mixture composed of a mineral acid (a1) and a thiol (a2), the mineral acid (a1) being a hydrogen chloride gas and the thiol (a2) being an alkylmercaptan having 1 to 12 carbon atoms.

8. The process as claimed in claim 1, wherein the phenol (A) is phenol.

* * * * *